US012544507B2

(12) United States Patent
Choy et al.

(10) Patent No.: US 12,544,507 B2
(45) Date of Patent: Feb. 10, 2026

(54) IMPLANTABLE MANUALLY-CONTROLLABLE DRUG DELIVERY APPARATUS

(71) Applicant: TOBIOS CORPORATION, Seoul (KR)

(72) Inventors: Young Bin Choy, Seoul (KR); Seung Ho Lee, Seoul (KR); Yong Chan Cho, Seoul (KR); Cho Rim Kim, Seoul (KR)

(73) Assignee: TOBIOS CORPORATION, Seoul (KR)

( * ) Notice: Subject to any disclaimer, the term of this patent is extended or adjusted under 35 U.S.C. 154(b) by 802 days.

(21) Appl. No.: 17/759,603

(22) PCT Filed: Nov. 13, 2020

(86) PCT No.: PCT/KR2020/015827
§ 371 (c)(1),
(2) Date: Jul. 27, 2022

(87) PCT Pub. No.: WO2021/153882
PCT Pub. Date: Aug. 5, 2021

(65) Prior Publication Data

US 2023/0052814 A1 Feb. 16, 2023

(30) Foreign Application Priority Data

Jan. 28, 2020 (KR) ........................ 10-2020-0009763

(51) Int. Cl.
*A61M 5/168* (2006.01)
*A61M 5/142* (2006.01)

(52) U.S. Cl.
CPC ............ *A61M 5/168* (2013.01); *A61M 5/142* (2013.01); *A61M 2205/8281* (2013.01)

(58) Field of Classification Search
CPC ........... A61M 2005/14506; A61M 2205/8281; A61M 5/1452; A61M 5/14546;
(Continued)

(56) References Cited

U.S. PATENT DOCUMENTS 4,761,158 A * 8/1988 Schulte ............... A61M 5/1428 604/9
4,766,889 A 8/1988 Trick et al.
(Continued)

FOREIGN PATENT DOCUMENTS

CN 101351240 A 1/2009
DE 3639980 C * 5/1988 .......... A61M 5/1428
(Continued)

OTHER PUBLICATIONS

Extended European Search Report for EP 20916580.2 by European Patent Office dated Jan. 4, 2024.
(Continued)

*Primary Examiner* — Rebecca E Eisenberg
(74) *Attorney, Agent, or Firm* — BROADVIEW IP LAW, PC

(57) ABSTRACT

The present disclosure relates to an implantable drug delivery device including a manual control actuator that allows a patient to self-administer a fixed amount of a drug at a desired time. By controlling a drug level, the volume inside a drug chamber, the number of actuations, and the like, a device of the present disclosure allows a drug to be precisely controlled and delivered from the outside after the device is implanted in vivo, and thus it is convenient to control a drug administration schedule. Also, since a battery is not required, and internal control devices for electromagnetic control become unnecessary, it is more patient-friendly and economically feasible.

6 Claims, 9 Drawing Sheets

(58) Field of Classification Search
CPC ............ A61M 5/14276; A61M 5/1428; A61M 5/1413; A61M 5/14212; A61M 5/14216
See application file for complete search history.

(56) References Cited

U.S. PATENT DOCUMENTS

| | | | | |
|---|---|---|---|---|
| 5,785,681 | A * | 7/1998 | Indravudh ............. | A61M 5/141 604/65 |
| 5,895,372 | A | 4/1999 | Zenner et al. | |
| 7,052,488 | B2 | 5/2006 | Uhland | |
| 8,172,800 | B2 | 5/2012 | Rush et al. | |
| 2003/0032947 | A1 * | 2/2003 | Harper .................. | A61M 5/145 604/892.1 |
| 2006/0122578 | A1 | 6/2006 | Lord et al. | |
| 2010/0049132 | A1 | 2/2010 | Rush et al. | |
| 2013/0345633 | A1 * | 12/2013 | Chong .................. | A61M 5/145 604/134 |
| 2017/0119961 | A1 | 5/2017 | Forsell | |

FOREIGN PATENT DOCUMENTS

| | | | | |
|---|---|---|---|---|
| JP | 2009-514580 | A | 4/2009 | |
| KR | 10-2012-0130884 | A | 12/2012 | |
| KR | 10-1445975 | B1 | 9/2014 | |
| KR | 10-2017-0128811 | A | 11/2017 | |
| KR | 10-2018-0095316 | A | 8/2018 | |
| WO | WO-2011126569 | A1 * | 10/2011 | ............. A45D 34/00 |

OTHER PUBLICATIONS

Office Action for CN 202080094941.X by China National Intellectual Property Administration dated Feb. 21, 2024.
International Search Report for PCT/KR2020/125827 by Korean Intellectual Property Office dated Jun. 2, 2021.
Office Action for JP 2022-546455 by Japan Patent Office dated Aug. 8, 2023.
Office Action for CN 202080094941.X by China National Intellectual Property Administration dated May 27, 2023.
International Search Report for PCT/KR2020/015827 by Korean Intellectual Property Office dated Jun. 2, 2021.

* cited by examiner

IMPLANTABLE MANUALLY-CONTROLLABLE DRUG DELIVERY APPARATUS

CROSS-REFERENCE TO RELATED APPLICATIONS

This application is a National Phase Entry Application of PCT Application No. PCT/KR2020/015827 filed on Nov. 13, 2020, which claims priority to Korean Patent Application No. 10-2020-0009763 filed on Jan. 28, 2020, in Korean Intellectual Property Office, the entire contents of which are hereby incorporated by reference in its entirety.

TECHNICAL FIELD

The present disclosure relates to a drug delivery technology for implantation in vivo, and more particularly, to an implantable drug delivery device including a manual control actuator that allows a patient to self-administer a fixed amount of a drug at a desired time.

BACKGROUND ART

Long-term, continuous drug therapy is necessary for treating patients with chronic diseases such as cancer, neurological diseases, diabetes, or osteoporosis. As one type of drug therapy, chronotherapy which is a method in which a drug is precisely injected at a specific time slot to increase absorption of the drug and minimize side effects has been used. Specifically, in chronotherapy, 1) oral administration; 2) injections; and 3) implantable devices have been used.

Among the above, regarding oral administration, due to a problem that a drug used for a chronic disease is denatured or deactivated as it passes through a gastrointestinal tract, there are disadvantages that bioavailability of the drug is low and side effects due to the exposure of the drug to the gastrointestinal tract are severe. Regarding injections, despite being highly effective, a patient may be under a lot of stress due to an increased number of administrations to maintain a constant drug level in the blood for a long period of time. Also, regarding implantable devices that deliver a drug by a sustained release through diffusion of the drug, although long-term drug delivery is possible, there is a problem that the drug is rapidly released immediately after implantation of the device, or the amount of the drug released cannot be controlled after the implantation of the device. Implantable devices for overcoming such problems have a battery, an electronic circuit, or the like mounted therein to control drug release, and thus the volume is increased, and additional implantation surgery may be required due to a battery replacement problem in some cases.

U.S. Pat. No. 7,052,488 relates to an implantable drug delivery device and discloses a pulse-type drug delivery technology that can be controlled on the basis of a plurality of drug storages. In a state in which each drug storage is filled with a drug and the top of each drug storage is sealed with gold foil, the gold foil is mechanically ruptured to release the drug. However, the device has problems that components increasing the volume, such as a controller and a battery, are added into the device to rupture the gold foil, and reinjection of the drug is impossible.

Therefore, in order to overcome such problems, there is a demand for the development of an implantable drug delivery device that does not require any internal attachment or a battery so that size reduction is possible, and that allows for precise control of an amount of a drug administered and a drug administration schedule according to a patient's needs from the outside even after implantation in vivo.

RELATED ART DOCUMENT

Patent Document (Patent Document 1) U.S. Pat. No. 7,052,488

DISCLOSURE

Technical Problem

The present disclosure provides a drug delivery device that does not require any internal attachment or a battery so that size reduction is possible, and that is manually controlled by a patient to control an amount of a drug administered and a drug administration schedule from an outside even after implantation in vivo.

Technical Solution

One embodiment of the present disclosure provides an implantable manual control drug delivery device including a drug storage configured to be filled with and store a drug, a drug release actuator configured to release the drug of the drug storage in predetermined amounts to an outside of the device through movement of a manual control button, and a housing in which the drug storage and the drug release actuator are stacked and which constitutes an external form of the device, wherein a drug injection port and a drug delivery port are formed in a space of the housing in which the drug storage is stacked, a space of the housing in which the drug release actuator is stacked includes an actuator space which includes an opening for vertical movement of a spring actuator configured to pump the drug and a drug chamber space which is configured to be filled with a predetermined amount of the drug as the drug is pumped and then release the drug, the drug release actuator includes an inlet valve configured to connect the drug storage and the drug chamber space, a drug chamber connected to one end of the inlet valve, an outlet valve configured to connect the drug chamber and a drug discharge port, and the spring actuator connected to the manual control button and configured to apply a pressure to the drug chamber, and due to the movement of the manual control button, the spring actuator releases a drug of the drug chamber to the outside of the device through the outlet valve and the drug discharge port and fills the drug chamber with the drug of the drug storage through the inlet valve.

The spring actuator may include a piston configured to come in contact with the drug chamber, a spring configured to apply a restoration force to a position at which the piston does not apply a pressure to the drug chamber, and the manual control button moved so that, against the restoration force of the spring, the spring moves to a position at which the piston applies the pressure to the drug chamber.

The spring actuator may further include a piston actuation force controller, and the piston actuation force controller may include a notch formed on a housing fixer configured to support the piston, a guide window formed to be inclined on the manual control button, a latch configured to pass through the notch and move along the guide window and formed on the piston in a direction perpendicular to a movement direction of the piston to control the movement of the piston along a direction of the notch, an inner spring which constitutes the spring and is configured to, in response to the manual control button being pressed, push the piston downward in response to the latch moving along the guide window, horizontally moving in the notch, and then reaching a broken part of the notch, and an outer spring which constitutes the spring and is configured to, in response to a force pressing the manual control button being removed, return the manual control button to its original position and, in that process, horizontally move and return the latch to a position before application of the pressing force in response to the latch moving along the guide window, vertically moving in the notch, and then reaching the broken part of the notch.

The drug storage may include a drug reservoir configured to deliver the drug injected through the drug injection port to the inlet valve.

The drug reservoir, a drug injection port connection tube, and an inlet valve connection tube may be included in an integrated form in the space of the housing in which the drug storage is stacked, and the inlet valve and the outlet valve may be included in an integrated form in the space of the housing in which the drug release actuator is stacked.

The spring actuator may release the drug during vertical movement.

The drug storage and the drug release actuator may be disposed in parallel with each other inside the housing, and the drug delivery port, the inlet valve, the drug chamber, and the outlet valve may be arranged in one straight line.

The drug storage and the drug release actuator may be disposed in series with each other inside the housing, the drug delivery port, the inlet valve, and the drug chamber may be arranged in one straight line, and a direction in which the drug chamber and the outlet valve are connected may be formed as a direction different from the straight line.

Advantageous Effects

By controlling a drug level, the volume inside a drug chamber, the number of actuations, and the like, a device of the present disclosure allows a drug to be precisely controlled and delivered from the outside after the device is implanted in vivo, and thus it is convenient to control a drug administration schedule. Also, since an external power source, such as a battery, is not required, and internal control devices for electromagnetic control become unnecessary, it is more economically feasible. In addition, since it is possible to always push a piston with the same pressure just by pressing a spring actuator to a predetermined depth or more, the drug can be released in fixed amounts.

MODES OF THE INVENTION

Figure 1:
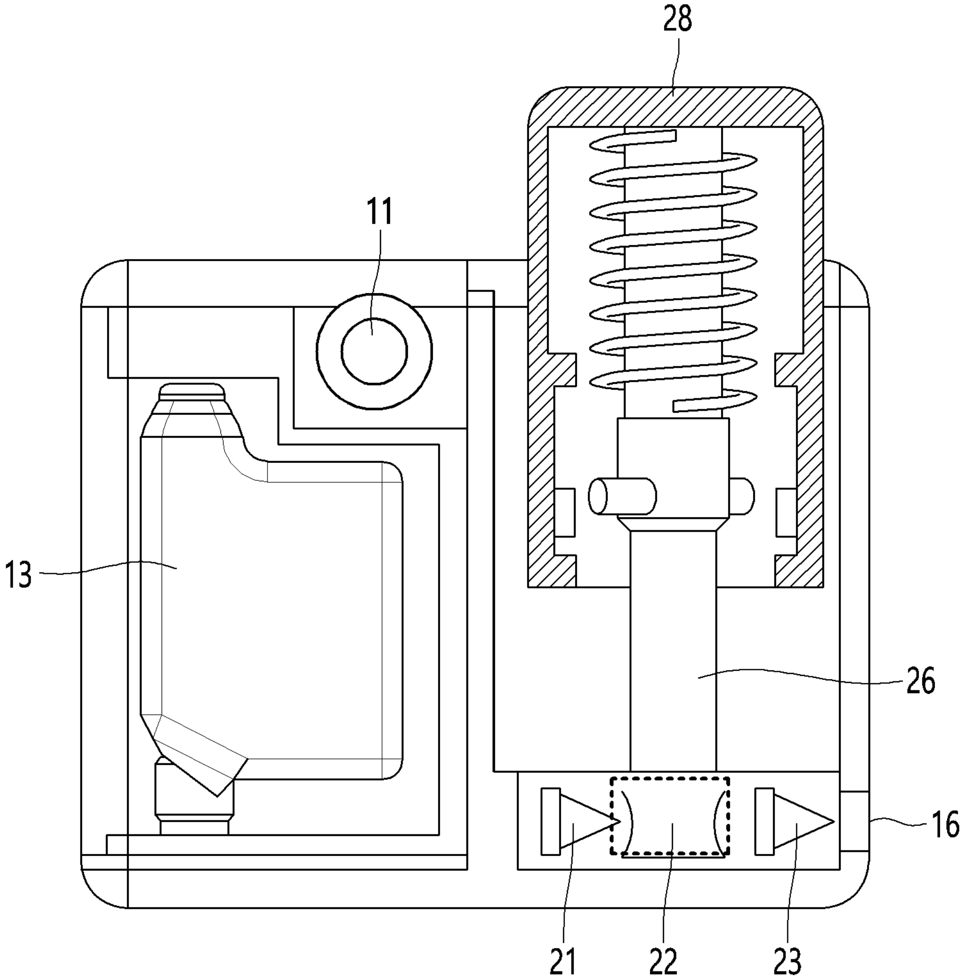
FIG. 1 is a conceptual diagram of an implantable manual control drug delivery device according to a first embodiment of the present disclosure.

Prior to the detailed description of the present disclosure, note that the terms or words used in the present specification and claims described below should not be construed as being limited to general or dictionary meanings thereof. Accordingly, the embodiments described in this specification and configurations illustrated in the drawings are only exemplary embodiments of the present disclosure and do not represent the entire technical spirit of the present disclosure, and thus, it should be understood that various equivalents and modifications that may substitute therefor may be present at the time of filing this application.

Here, in all of the drawings for describing the embodiments of the present disclosure, components having the same functions are denoted by the same reference numerals, and detailed description thereof will be omitted. Hereinafter, the present disclosure will be described with reference to the accompanying drawings.

Figure 2:
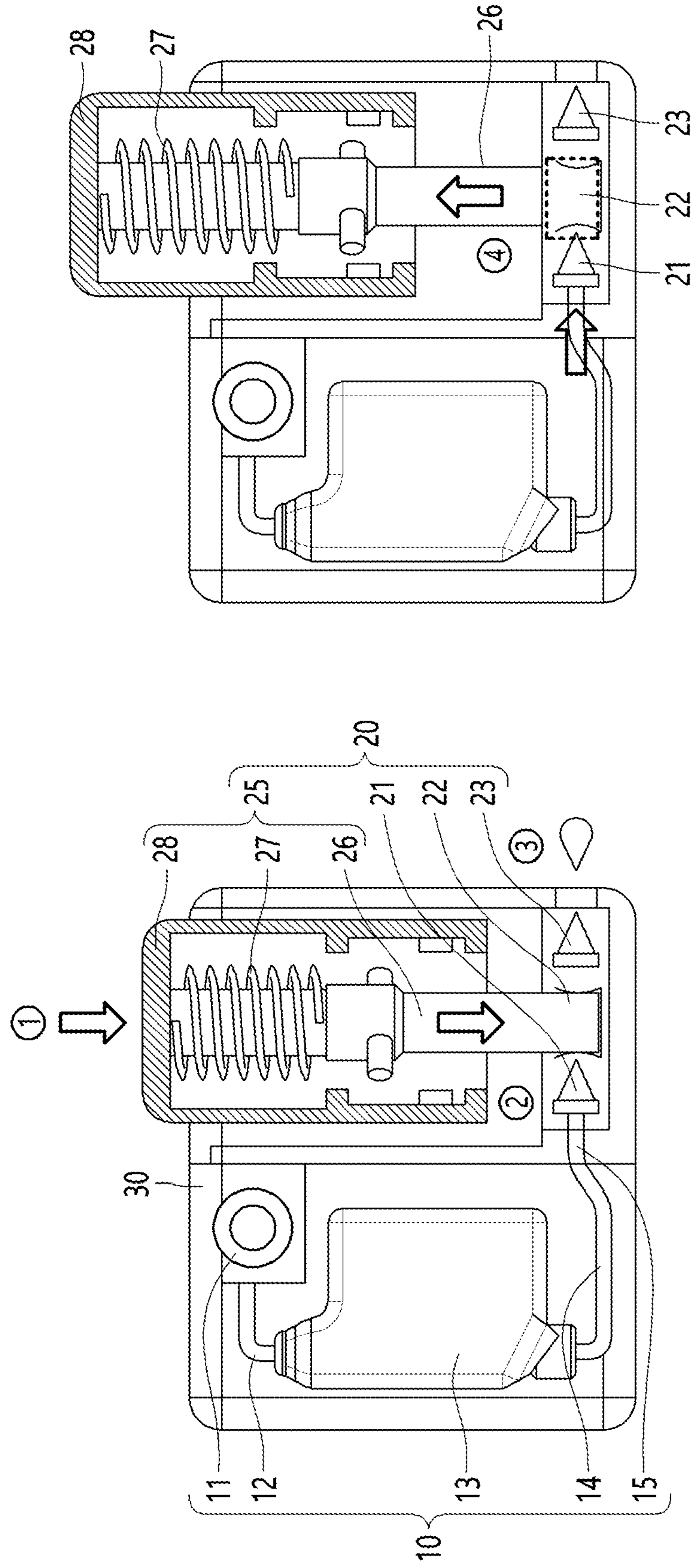
FIG. 2 is a conceptual diagram illustrating a drug release actuation of the implantable manual control drug delivery device according to the first embodiment of the present disclosure.

FIGS. 1 to 6 are conceptual diagrams of an implantable manual control drug delivery device having a parallel structure according to a first embodiment of the present disclosure. FIG. 1 is a conceptual diagram of the implantable manual control drug delivery device in which a drug storage and a drug release actuator of the implantable manual control drug delivery device of the present disclosure are disposed in parallel. FIG. 2 is a conceptual diagram illustrating a drug release actuation of the implantable manual control drug delivery device according to the first embodiment of the present disclosure. The implantable manual control drug delivery device according to one embodiment of the present disclosure includes a drug storage 10 configured to be filled with a drug and discharge the drug, a drug release actuator 20 configured to release the drug of the drug storage in predetermined amounts to an outside of the device, and a housing 30 in which the drug storage and the drug release actuator are spatially separated and stacked adjacent to each other and which constitutes an external form of the device. In one embodiment of the present disclosure, the drug storage 10 and the drug release actuator 20 may be disposed in parallel with each other inside the housing, and a drug delivery port, an inlet valve, a drug chamber, and an outlet valve may be arranged in one straight line.

The drug storage 10 of the housing 30 according to one embodiment of the present disclosure is a space configured to be filled with and store a drug and may include a drug injection port 11 formed on an outer wall surface and a drug delivery port 15 formed on an inner wall surface facing the drug release actuator. A space of the housing in which the drug release actuator 20 is stacked includes an actuator space which includes an opening for vertical movement of a spring actuator configured to pump the drug received from the drug delivery port 15 and a drug chamber 22 space which is configured to be filled with a predetermined amount of the drug as the drug is pumped and then release the drug to the outside. In one embodiment of the present disclosure, the drug injection port 11 may protrude from the housing 30 to allow a drug to be injected even after the device is implanted in vivo.

The drug storage 10 according to one embodiment of the present disclosure includes a drug reservoir 13 configured to receive a drug from the drug injection port 11 and deliver the drug to the drug delivery port 15, a drug injection port connection tube 12 configured to connect the drug injection port 11 and the drug reservoir 13, and a drug delivery port connection tube 14 configured to connect the drug reservoir 13 and the drug delivery port 15.

The drug release actuator 20 includes an inlet valve 21 which is connected to the drug delivery port 15 and allows the drug to advance in one direction, the drug chamber 22 whose one end is connected to a drug outlet of the inlet valve, an outlet valve 23 configured to connect the drug chamber and a drug discharge port 16 through which the drug is released to the outside of the device, and a spring actuator 25 configured to apply a pressure to the drug chamber 22 to release the drug of the drug chamber to the outlet valve 23 and remove the pressure from the drug chamber to fill the drug chamber 22 with the drug from the inlet valve 21. Due to movement of a manual control button, the spring actuator may release the drug of the drug chamber 22 to the outside of the device through the outlet valve 23 and the drug discharge port 16 and may fill the drug chamber 22 with the drug of the drug storage 10 through the inlet valve 21. The inlet valve 21 and the outlet valve 23 according to one embodiment of the present disclosure may be formed in the shape of a funnel to allow the drug to flow in one direction and may include a reverse flow prevention membrane formed at the drug outlet to prevent the drug from flowing in a direction opposite to an advancing direction thereof.

In the housing according to one embodiment of the present disclosure, the space in which the drug storage 10 is stacked may include the drug reservoir 13, the drug injection port connection tube 12, and the drug delivery port connection tube 14 in an integrated form, and the space in which the drug release actuator is stacked may include the inlet valve 21 and the outlet valve 23 in an integrated form.

The spring actuator 25 according to one embodiment of the present disclosure includes a piston 26 configured to come in contact with the drug chamber 22, a spring 27 configured to apply a restoration force to a position at which the piston does not apply a pressure to the drug chamber, and a manual control button 28 moved so that, against the restoration force of the spring, the spring moves to a position at which the piston applies the pressure to the drug chamber.

A drug release process through the actuation of the spring actuator 25 is as follows: 1) as the manual control button 28 is pressed, 2) the piston 26 inside the spring actuator 25 moves downward and pushes the drug filled in the drug chamber 22, and 3) the drug is released to the outside through the drug discharge port 16 through the outlet valve 23. Then, 4) due to a restoration force of the spring 27, the piston 26 returns to its original position, and here, the drug chamber 22 is refilled with the drug present in the drug reservoir 13 through the inlet valve 21.

In the first embodiment of the present disclosure, the spring actuator may further include a piston actuation force controller, and the piston actuation force controller may include a notch formed on a housing fixer configured to support the piston, a guide window formed to be inclined on the manual control button, a latch configured to pass through the notch and move along the guide window and formed on the piston in a direction perpendicular to a movement direction of the piston to control the movement of the piston along a direction of the notch, an inner spring which constitutes the spring and is configured to, in response to the manual control button being pressed, push the piston downward in response to the latch moving along the guide window, horizontally moving in the notch, and then reaching a broken part of the notch, and an outer spring which constitutes the spring and is configured to, in response to a force pressing the manual control button being removed, return the manual control button to its original position and, in that process, horizontally move and return the latch to a position before application of the pressing force in response to the latch moving along the guide window, vertically moving in the notch, and then reaching the broken part of the notch.

Figure 3:
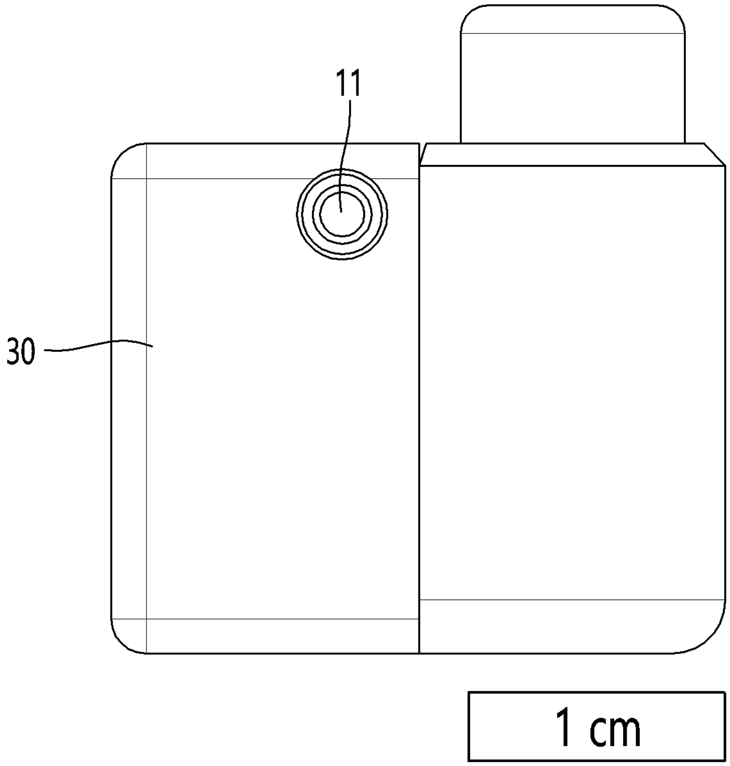
FIG. 3 illustrates an actual shape of the implantable manual control drug delivery device according to the first embodiment of the present disclosure.
Figure 4:
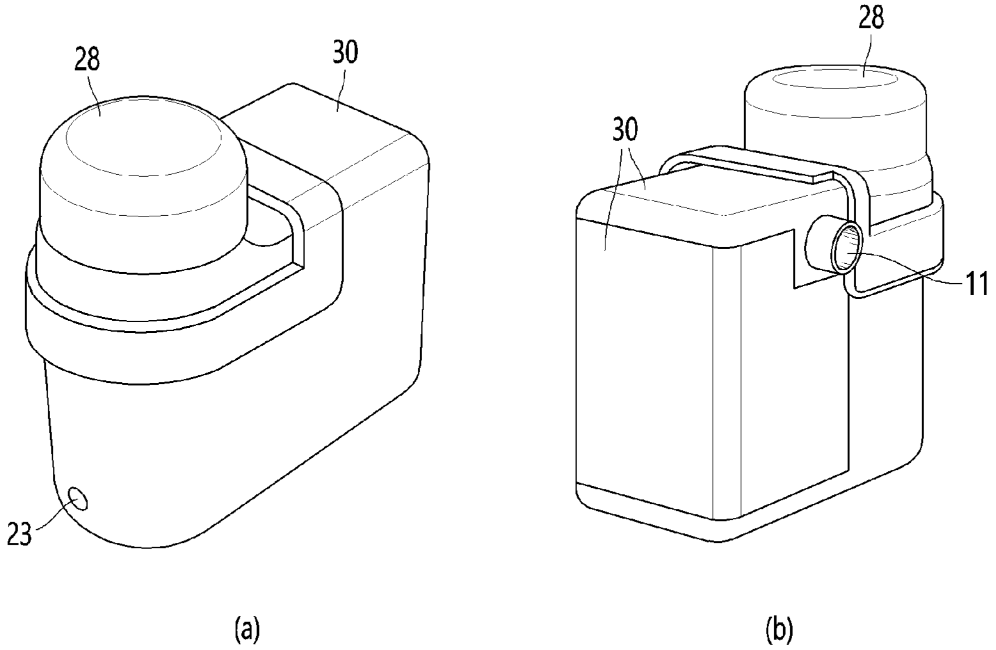
FIG. 4 is a conceptual diagram illustrating an exterior of the implantable manual control drug delivery device according to the first embodiment of the present disclosure.
Figure 5:
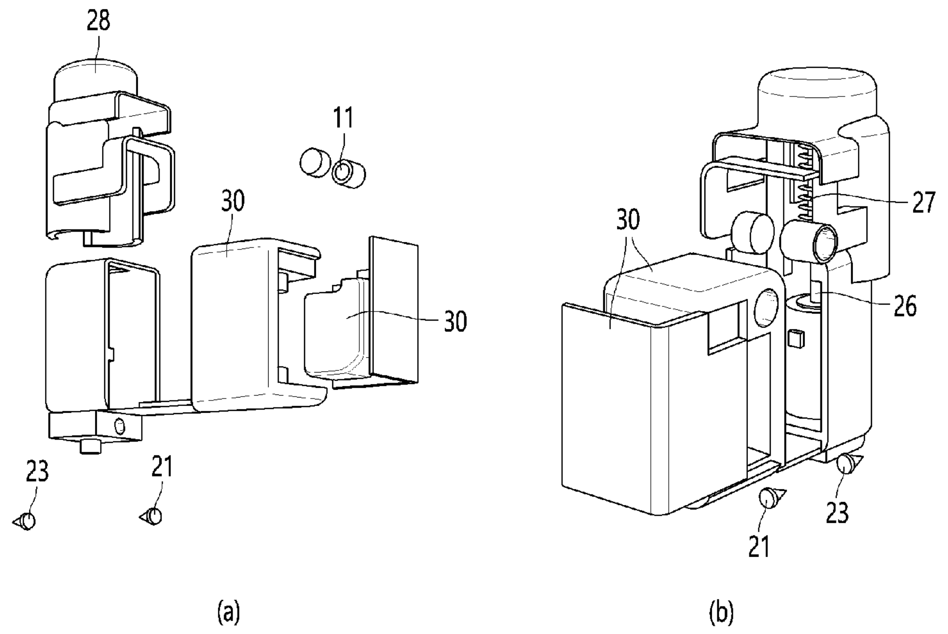
FIG. 5 is a conceptual diagram illustrating an exploded state of components of the implantable manual control drug delivery device according to the first embodiment of the present disclosure.
Figure 6:
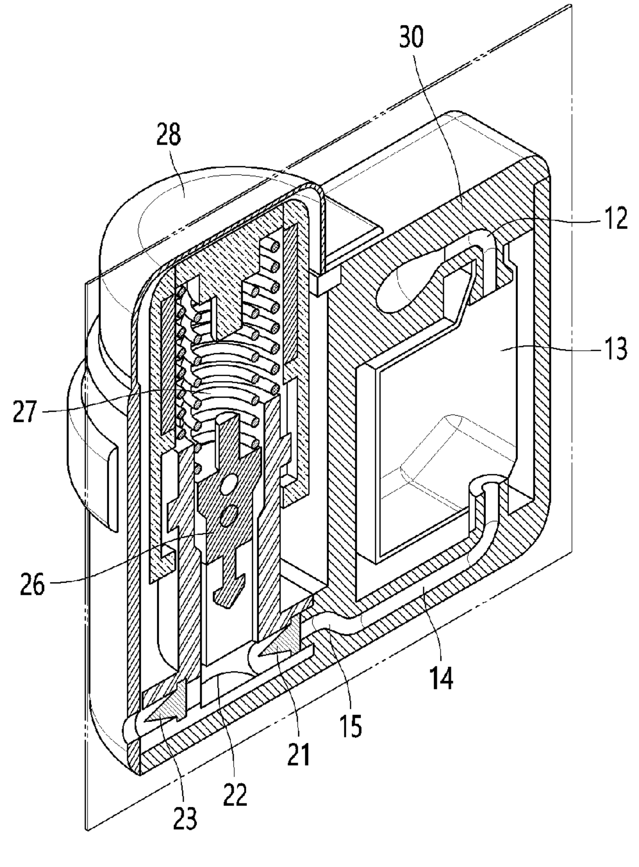
FIG. 6 is a conceptual diagram illustrating a cross-section of the inside of the implantable manual control drug delivery device according to the first embodiment of the present disclosure.

FIG. 3 illustrates an actual shape of the implantable manual control drug delivery device according to the first embodiment of the present disclosure, and FIG. 4 illustrates an exterior of the implantable manual control drug delivery device according to the first embodiment of the present disclosure. Also, FIG. 5 illustrates an exploded state of components of the implantable manual control drug delivery device according to the first embodiment of the present disclosure, and FIG. 6 illustrates a cross-section of the inside of the implantable manual control drug delivery device according to the first embodiment of the present disclosure. Actual structures that correspond to individual components of FIGS. 1 and 2 are indicated with reference numerals thereof.

Figure 7:
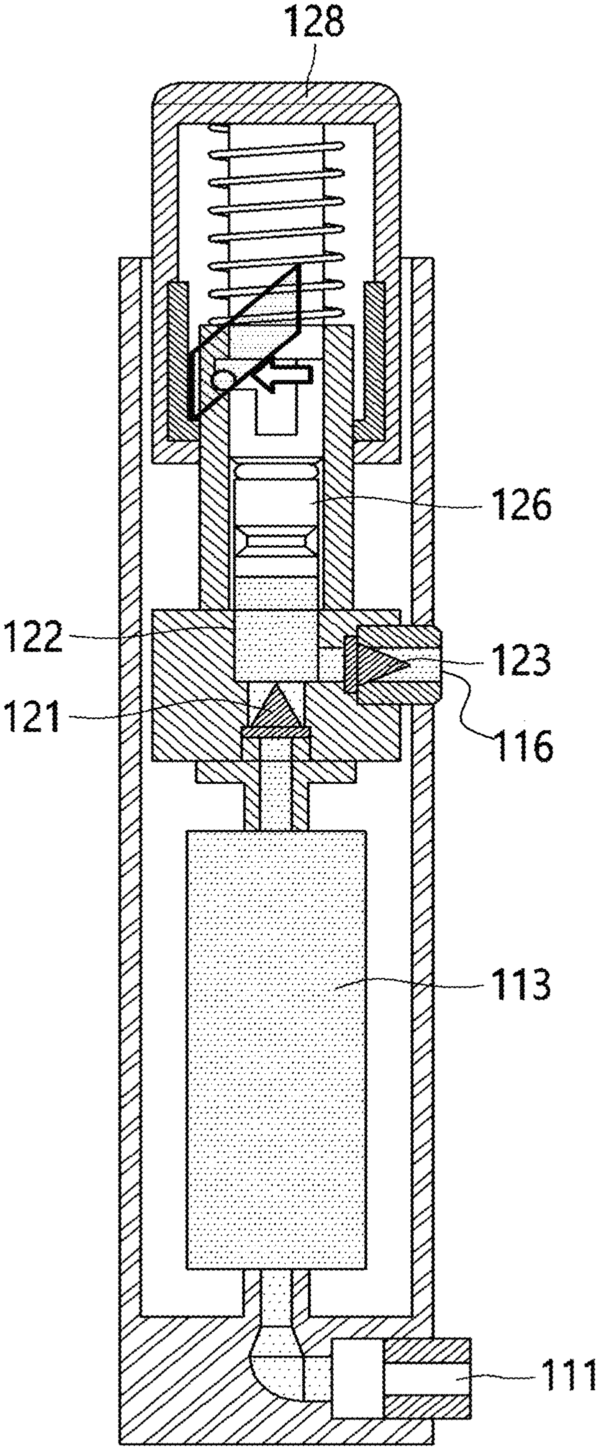
FIG. 7 is a conceptual diagram of an implantable manual control drug delivery device according to a second embodiment of the present disclosure.
Figure 8:
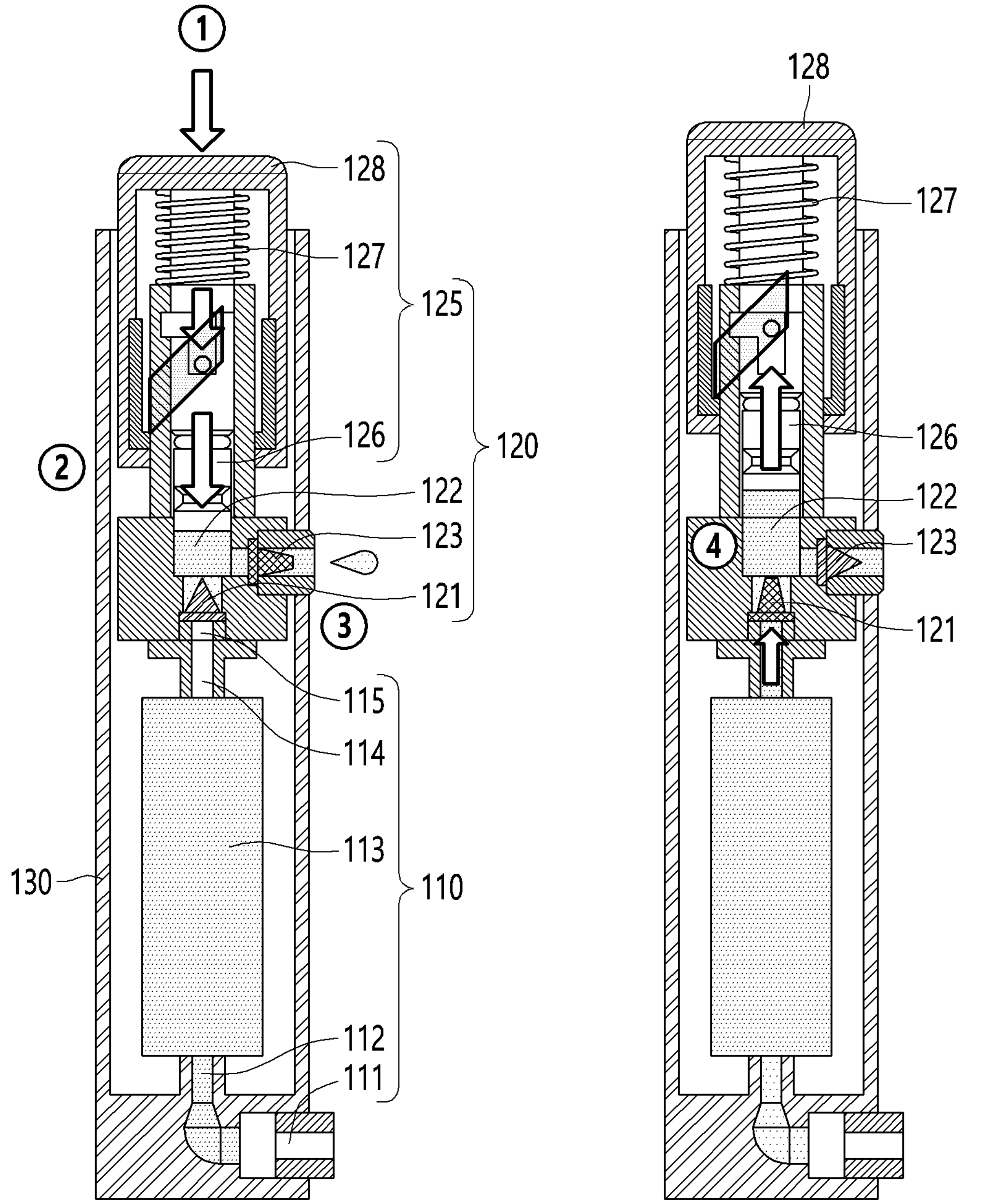
FIG. 8 is a conceptual diagram illustrating a drug release actuation of the implantable manual control drug delivery device according to the second embodiment of the present disclosure.

FIGS. 7 to 10 are conceptual diagrams of an implantable manual control drug delivery device according to a second embodiment of the present disclosure and relate to a serial-type drug delivery device. FIG. 7 is a conceptual diagram of an implantable manual control drug delivery device in which a drug storage and a drug release actuator are disposed in series. In one embodiment of the present disclosure, a drug storage 110 and a drug release actuator 120 may be disposed in series with each other inside a housing 130, a drug delivery port 115, an inlet valve 121, and a drug chamber 122 may be arranged in one straight line, and a direction in which the drug chamber 122 and an outlet valve 123 are connected may be formed as a direction different from the straight line. In one embodiment, a direction in which the drug delivery port 115, the inlet valve 121, and the drug chamber 122 are connected may be orthogonal to the direction in which the drug chamber 122 and the outlet valve 123 are connected, and thus a direction of a drug outlet of the inlet valve 121 and a direction of a drug outlet of the outlet valve 123 may also be orthogonal to each other. FIG.

8 is a conceptual diagram illustrating a drug release actuation of the implantable manual control drug delivery device according to the second embodiment of the present disclosure. The implantable manual control drug delivery device according to one embodiment of the present disclosure includes the drug storage 110 configured to be filled with a drug and discharge the drug, the drug release actuator 120 configured to release the drug of the drug storage in predetermined amounts to the outside of the device, and the housing 130 in which the drug storage and the drug release actuator are spatially separated and stacked adjacent to each other and which constitutes an external form of the device.

In the housing 130 according to one embodiment of the present disclosure, a space of the housing 130 in which the drug storage 110 is stacked includes a drug injection port 111 formed on an outer wall surface and the drug delivery port 115 formed on an inner wall surface facing the drug release actuator, and a space of the housing in which the drug release actuator 120 is stacked includes an actuator space which includes an opening for vertical movement of a spring actuator configured to pump the drug received from the drug delivery port 115 and a drug chamber 122 space which is configured to be filled with a predetermined amount of the drug as the drug is pumped and then release the drug. In one embodiment of the present disclosure, the drug injection port 111 may protrude from the housing 130 to allow a drug to be injected even after the device is implanted in vivo.

The drug storage 110 according to one embodiment of the present disclosure includes a drug reservoir 113 configured to receive a drug from the drug injection port 111 and deliver the drug to the drug delivery port 115, a drug injection port connection tube 112 configured to connect the drug injection port 111 and the drug reservoir 113, and a drug delivery port connection tube 114 configured to connect the drug reservoir 113 and the drug delivery port. The drug release actuator 120 includes the inlet valve 121 which is connected in series to the drug delivery port 115 and allows the drug to advance in one direction, the drug chamber 122 whose one end is connected to the drug outlet of the inlet valve, the outlet valve 123 configured to connect the drug chamber and a drug discharge port 116, and a spring actuator 125. The spring actuator may apply a pressure to the drug chamber 122 to deliver the drug of the drug chamber to the outlet valve 123 and release the drug to the outside of the device through the drug discharge port 116, and may remove the pressure from the drug chamber to fill the drug chamber 122 with the drug from the inlet valve 121. The inlet valve 121 and the outlet valve 123 according to one embodiment of the present disclosure may be formed in the shape of a funnel to allow the drug to flow in one direction and may include a reverse flow prevention membrane formed at the drug outlet to prevent the drug from flowing in a direction opposite to an advancing direction thereof.

In the housing according to one embodiment of the present disclosure, the space in which the drug storage 110 is stacked may include the drug reservoir 113, the drug injection port connection tube 112, and the drug delivery port connection tube 114 in an integrated form, and the space in which the drug release actuator is stacked may include the inlet valve 121 and the outlet valve 123 in an integrated form. The spring actuator 125 according to one embodiment of the present disclosure includes a piston 126 configured to come in contact with the drug chamber 122, a spring 127 configured to apply a restoration force to a position at which the piston does not apply a pressure to the drug chamber, and a manual control button 128 moved so that, against the restoration force of the spring, the spring moves to a position at which the piston applies the pressure to the drug chamber.

A drug release process through the actuation of the spring actuator 125 is as follows: 1) as the manual control button 128 is pressed, 2) the piston 126 inside the spring actuator 125 moves downward and pushes the drug filled in the drug chamber 122, and 3) the drug is released to the outside through the outlet valve 123. Then, 4) due to a restoration force of the spring 127, the piston 126 returns to its original position, and here, the drug chamber 122 is refilled with the drug present in the drug reservoir 113 through the inlet valve 121.

Figure 9:
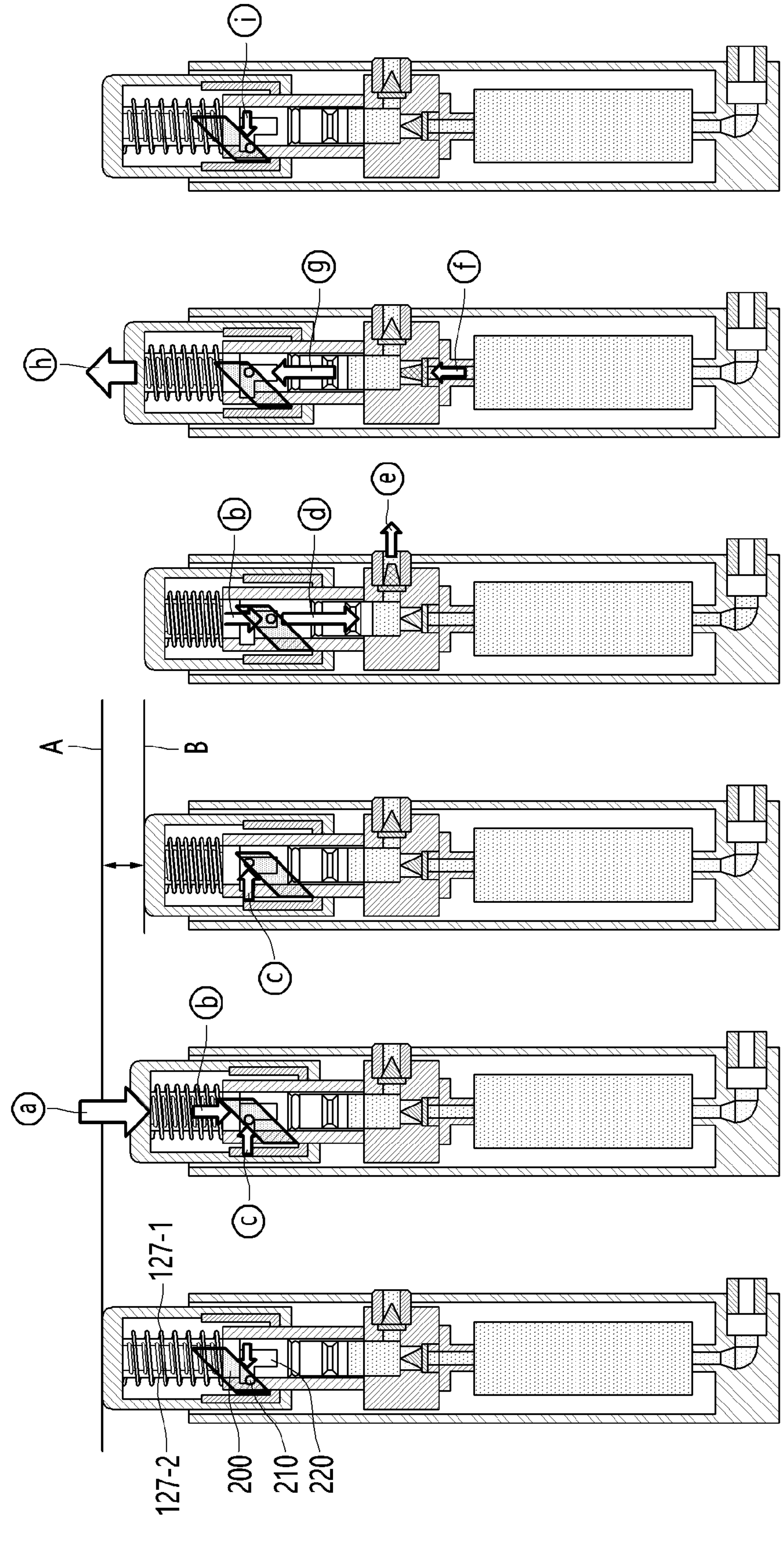
FIG. 9 is a conceptual diagram illustrating a drug release actuation of the implantable manual control drug delivery device having a piston actuation force control function according to the second embodiment of the present disclosure.
Figure 10:
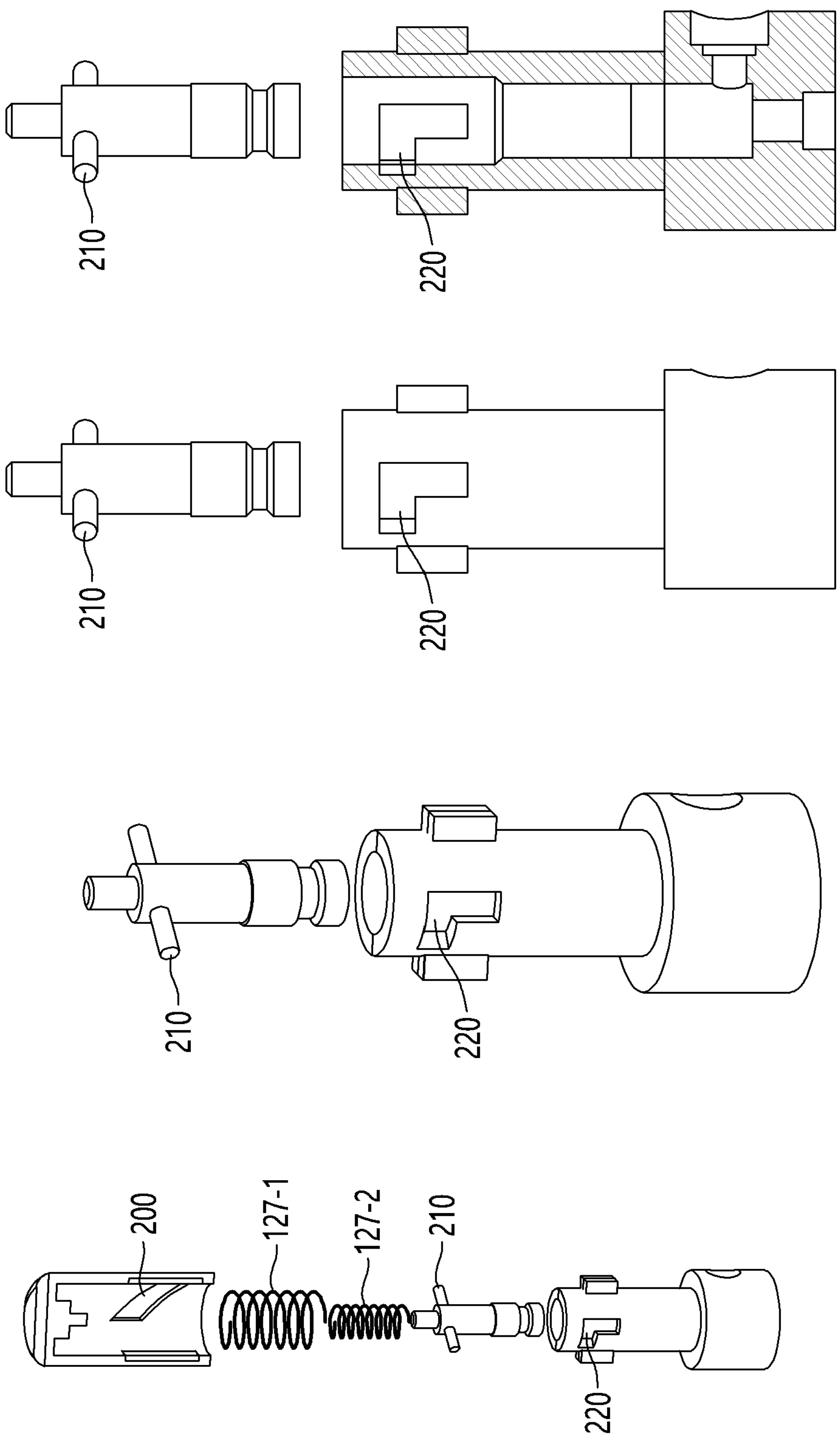
FIG. 10 is an exploded perspective view of a piston actuation force controller according to the second embodiment of the present disclosure.

FIG. 9 is a conceptual diagram illustrating a drug release actuation of the implantable manual control drug delivery device having a piston actuation force control function according to the second embodiment of the present disclosure, and FIG. 10 is an exploded perspective view of a piston actuation force controller according to the second embodiment of the present disclosure. In one embodiment of the present disclosure, the spring actuator may further include a piston actuation force controller, and the piston actuation force controller may include a notch 220 formed in an L-shape on a housing fixer configured to support the piston, a guide window 200 formed to be inclined on the manual control button, a latch 210 configured to pass through the notch and move along the guide window and formed on the piston in a direction perpendicular to a movement direction of the piston to control the movement of the piston along a direction of the notch, an inner spring 127-2 which constitutes the spring and is configured to, in response to the manual control button being pressed, push the piston downward in response to the latch moving along the guide window, horizontally moving in the notch, and then reaching a broken part of the notch, and an outer spring 127-1 which constitutes the spring and is configured to, in response to a force pressing the manual control button being removed, return the manual control button to its original position and, in that process, horizontally move and return the latch to a position before application of the pressing force in response to the latch moving along the guide window, vertically moving in the notch, and then reaching the broken part of the notch.

In one embodiment of the present disclosure, the manual control button 128 of the spring actuator 125 may not be actuated unless pressed to a predetermined depth or more and may always push the piston 126 with the same force only when pressed to the predetermined depth or more. To this end, the spring 127 of the spring actuator 125 includes the outer spring 127-1 and the inner spring 127-2, the outer spring 127-1 returns the manual control button 128 to its original position, and the inner spring 127-2 pushes the piston 126 downward. The latch 210 is formed on the piston 126 in a direction perpendicular to a movement direction of the piston. In a state in which the piston is not actuated, the latch 210 is caught in the notch 220 of the housing fixer configured to support the piston, and accordingly, even when the inner spring 127-2 pushes the piston, the piston does not move and thus does not apply a pressure to the drug chamber 122. An operational principle thereof will be described below.

A drug release actuation process of the implantable manual control drug delivery device having the piston actuation force control function is illustrated in detail in FIG. 9. The latch 210 protrudes past the notch 220, and a position of the latch 210 is restricted so that the latch 210 can move only along the guide window 200 formed to be inclined on the manual control button 128. a) As the manual control button 128 is pressed, b) the inner spring 127-2 is pressed, and c) the latch 210 moves along the guide window 200, but since the latch 210 is not able to deviate from a horizontal direction of the notch 220, the piston 126 does not apply a pressure to the drug chamber 122. Until a position of an upper surface of the manual control button 128 moves from A to B, the state in which the piston 126 does not apply a pressure to the drug chamber 122 is maintained due to the latch. d) As the latch 210 continues to move along the guide window 200, and the position of the upper surface of the manual control button 128 moves past B, the latch 210 reaches a vertical opening of the notch, and a limit on movement of the inner spring is released, causing the piston 126 to start moving and always apply a uniform pressure with the same force to the drug chamber 122. e) Upon receiving the pressure, the drug chamber releases a fixed amount of drug to the outlet valve 123. h) As the force pressing the manual control button 128 is removed, g) the piston 126 returns to its original position due to a force caused by the outer spring 127-1 being restored from a pressed state, and f) the drug chamber 122 is refilled with the drug as the inlet valve 121 is opened. In this process, i) the latch 210 moves along the horizontal direction of the notch 220 while moving along the guide window 200. By the above operation, the spring actuator 125 having the piston actuation force control function is operated only when pressed to a predetermined depth or more, and since it is possible to always push the piston with the same pressure just by pressing the spring actuator 125 to a predetermined depth or more, the drug can be released in fixed amounts.

EXAMPLE

Figure 11:
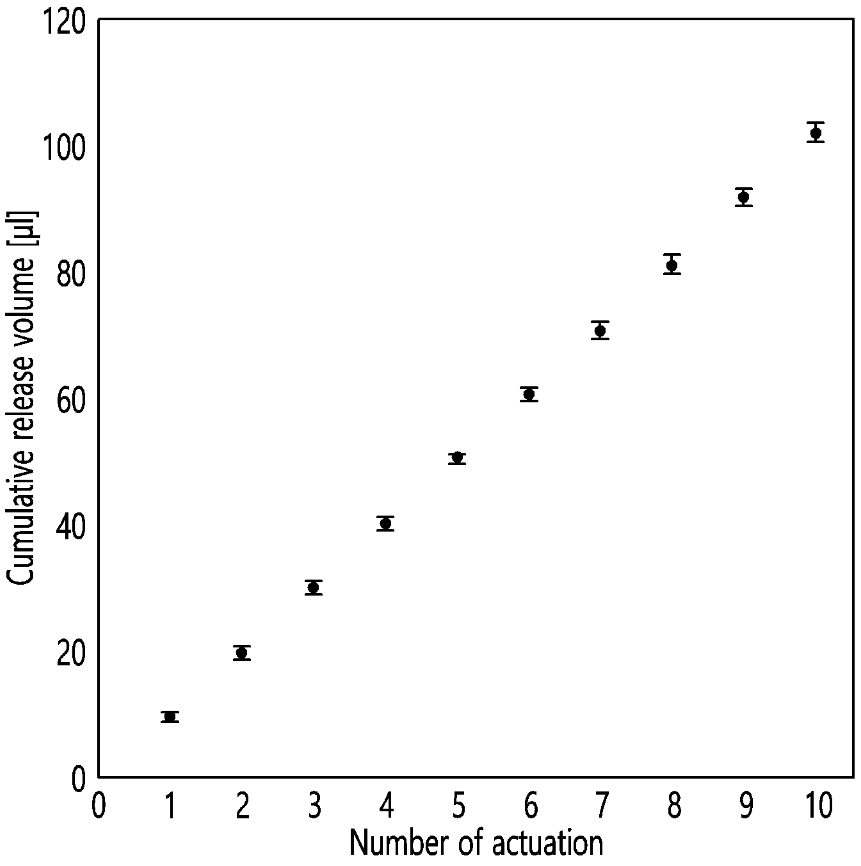
FIG. 11 is a graph showing a correlation between the number of times the implantable manual control drug delivery device of the present disclosure is used and the amount of a drug delivered.

FIG. 11 is a graph showing a correlation between the number of times the implantable manual control drug delivery device of the present disclosure is used and the amount of delivered drug. In order to test performance of the present device, drug injection performance was tested in vitro instead of being tested in vivo. As a result of testing an amount of injected drug according to a manually controlled number of pressing, it was confirmed that 10±1 μl of drug was injected during one compression.

The device according to the present disclosure may be implanted into various body parts or tissues of animals such as mammals, may be implanted into the body parts themselves that require treatment or parts such as subcutaneous parts or muscles that can deliver a drug to other parts through bodily functions, or may be implanted into an organ, an abdomen, or a forearm.

In this way, the device according to the present disclosure can be implanted into various parts of animals to deliver a drug. In another aspect, the present disclosure relates to a method of delivering a drug to a body part or an organ of an animal using the drug delivery device according to the present disclosure.

Exemplary embodiments of the present disclosure have been described above in detail, but the scope of the present disclosure is not limited thereto, and various modifications and improvements made by those of ordinary skill in the art using a basic concept of the present disclosure defined in the claims below also belong to the scope of the present disclosure.

Unless defined otherwise, all technical terms used in the present disclosure may have the same meaning as commonly understood by those of ordinary skill in the art to which the present disclosure pertains. The contents of all publications incorporated herein by reference are incorporated into the present disclosure.

DESCRIPTION OF REFERENCE NUMERALS

10, 110. Drug storage
11, 111. Drug injection port
12, 112. Drug injection port connection tube
13, 113. Drug reservoir
14, 114. Drug delivery port connection tube
15, 115. Drug delivery port
16, 116. Drug discharge port
20, 120. Drug release actuator
21, 121. Inlet valve
22, 122. Drug chamber
23, 123. Outlet valve
25, 125. Spring actuator
26, 126. Piston
27, 127. Spring
127-1. Outer spring
127-2. Inner spring
200. Guide window
210. Latch
220. Notch
28, 128. Manual control button
30, 130. Housing 1) Manual control button 28 or 128 is pressed
2) Piston 26 or 126 moves downward
3) Drug is released through outlet valve 23 or 123
4) Due to restoration force of spring 27 or 127, drug chamber 22 or 122 is refilled with drug a) Manual control button 128 is pressed
b) Inner spring 127-2 is also pressed
c) Latch 210 moves along guide window 200, but since latch 210 is not able to deviate from horizontal direction of notch 220, piston 126 does not apply pressure to drug chamber 122
d) As latch 210 continues to move along guide window 200, and position of upper surface of manual control button 128 moves past B, latch 210 reaches vertical opening of notch, and limit on movement of inner spring is released, causing piston 126 to start moving and always apply uniform pressure with same force to drug chamber 122
e) Upon receiving pressure, drug chamber releases fixed amount of drug to outlet valve 123
f) Drug chamber 122 is refilled with drug as inlet valve 121 is opened
g) Piston 126 returns to its original position due to force caused by outer spring 127-1 being restored from pressed state
h) Force pressing manual control button 128 is removed
i) Latch 210 moves along horizontal direction of notch 220 while moving along guide window 200

The invention claimed is:

1. An implantable manual control drug delivery device comprising:

a drug storage configured to be filled with and store a drug;

a drug release actuator configured to release the drug of the drug storage in predetermined amounts to the outside of the device through movement of a manual control button; and a housing in which the drug storage and the drug release actuator are stacked and which constitutes an external form of the device, wherein a drug injection port and a drug delivery port are formed in a space of the housing in which the drug storage is stacked, a space of the housing in which the drug release actuator is stacked includes an actuator space which includes an opening for vertical movement of a spring actuator configured to pump the drug and a drug chamber space which is configured to be filled with a predetermined amount of the drug as the drug is pumped and then release the drug, the drug release actuator includes an inlet valve configured to connect the drug storage and the drug chamber space, a drug chamber connected to one end of the inlet valve, an outlet valve configured to connect the drug chamber and a drug discharge port, and the spring actuator connected to the manual control button and configured to apply a pressure to the drug chamber, and due to the movement of the manual control button, the spring actuator releases a drug of the drug chamber to the outside of the device through the outlet valve and the drug discharge port and fills the drug chamber with the drug of the drug storage through the inlet valve, wherein the spring actuator includes:

a piston configured to come in contact with the drug chamber;

a spring comprising an inner spring and an outer spring configured to apply a restoration force to a position at which the piston does not apply a pressure to the drug chamber;

the manual control button moved so that, against the restoration force of the spring, the spring moves to a position at which the piston applies the pressure to the drug chamber; and a piston actuation force controller, wherein the piston actuation force controller includes:

a notch formed on a housing fixer which is configured to support the piston;

a guide window formed to be inclined on the manual control button;

a latch configured to pass through the notch and move along the guide window and formed on the piston in a direction perpendicular to a movement direction of the piston to control the movement of the piston along a direction of the notch;

the inner spring configured to, in response to the manual control button being pressed, push the piston downward in response to the latch moving along the guide window, horizontally moving in the notch, and then reaching a broken part of the notch; and the outer spring configured to, in response to a force pressing the manual control button being removed, return the manual control button to its original position and, in that process, horizontally move and return the latch to a position before application of the pressing force in response to the latch moving along the guide window, vertically moving in the notch, and then reaching the broken part of the notch.

2. The implantable manual control drug delivery device of claim 1, wherein the drug storage includes a drug reservoir configured to deliver the drug injected through the drug injection port to the inlet valve.

3. The implantable manual control drug delivery device of claim 2, wherein:

the drug reservoir, a drug injection port connection tube, and an inlet valve connection tube are included in an integrated form in the space of the housing in which the drug storage is stacked; and the inlet valve and the outlet valve are included in an integrated form in the space of the housing in which the drug release actuator is stacked.

4. The implantable manual control drug delivery device of claim 1, wherein the spring actuator releases the drug during vertical movement.

5. The implantable manual control drug delivery device of claim 1, wherein:

the drug storage and the drug release actuator are disposed in parallel with each other inside the housing; and the drug delivery port, the inlet valve, the drug chamber, and the outlet valve are arranged in one straight line.

6. The implantable manual control drug delivery device of claim 1, wherein:

the drug storage and the drug release actuator are disposed in series with each other inside the housing;

the drug delivery port, the inlet valve, and the drug chamber are arranged in one straight line; and a direction in which the drug chamber and the outlet valve are connected is formed as a direction different from the straight line.

* * * * *